United States Patent
Hynninen et al.

(10) Patent No.: US 10,188,868 B2
(45) Date of Patent: Jan. 29, 2019

(54) DEVICE SUPPORT APPARATUS

(71) Applicant: Nexstim Oy, Helsinki (FI)

(72) Inventors: Pentti Hynninen, Helsinki (FI); Gustaf Järnefelt, Helsinki (FI)

(73) Assignee: Nexstim Oyj, Helsinki (FI)

( * ) Notice: Subject to any disclaimer, the term of this patent is extended or adjusted under 35 U.S.C. 154(b) by 434 days.

(21) Appl. No.: 14/093,073

(22) Filed: Nov. 29, 2013

(65) Prior Publication Data
US 2015/0151137 A1   Jun. 4, 2015

(30) Foreign Application Priority Data
Nov. 29, 2013  (FI) .................................. 20136201

(51) Int. Cl.
*A61N 2/00* (2006.01)
*A61G 15/10* (2006.01)
*A61N 2/02* (2006.01)
*A61G 15/12* (2006.01)

(52) U.S. Cl.
CPC ........... *A61N 2/006* (2013.01); *A61G 15/125* (2013.01); *A61N 2/02* (2013.01)

(58) Field of Classification Search
CPC ......... A61N 2/006; A61N 2/02; A61G 15/125
USPC ......................................... 600/14; 248/354.6
See application file for complete search history.

(56) References Cited

U.S. PATENT DOCUMENTS

| | | | |
|---|---|---|---|
| 3,860,286 A * | 1/1975 | Rasmussen | A61G 15/125 297/408 |
| 3,877,751 A * | 4/1975 | Rasmussen | A47C 7/38 297/408 |
| 4,610,630 A | 9/1986 | Betush | |
| 6,210,317 B1 * | 4/2001 | Bonlie | A61N 2/02 600/9 |
| 6,254,532 B1 | 7/2001 | Paolitto et al. | |
| 6,288,785 B1 * | 9/2001 | Frantz | A61B 5/06 250/559.29 |
| 8,303,478 B2 | 11/2012 | Lebosse et al. | |
| 2004/0138524 A1 | 7/2004 | Ueda et al. | |
| 2004/0172012 A1 * | 9/2004 | Otsuka | 606/1 |
| 2005/0148808 A1 * | 7/2005 | Cameron | A61G 15/125 600/13 |
| 2005/0160532 A1 * | 7/2005 | Froelich | A61G 13/12 5/637 |
| 2005/0228209 A1 * | 10/2005 | Schneider | A61B 5/04009 600/13 |

(Continued)

FOREIGN PATENT DOCUMENTS

DE   102008034237 A1   2/2010
EP        1541110 A2   6/2005
(Continued)

*Primary Examiner* — Navin Natnithithadha
*Assistant Examiner* — Sunita Reddy
(74) *Attorney, Agent, or Firm* — Seppo Laine Oy

(57) ABSTRACT

According to an example embodiment of the present invention, there is provided an apparatus, comprising a first arm configured to accept a device, the first arm comprising a first counterweight arrangement, a second arm supporting the first arm by a coupling, and a base defining a curve and having the second arm mounted thereon, wherein the second arm is movable along the curve, the base configured to be mounted on a chair. The second arm may be furnished with a second counterweight arrangement.

21 Claims, 3 Drawing Sheets

(56) References Cited

U.S. PATENT DOCUMENTS

| | | | |
|---|---|---|---|
| 2005/0256539 A1* | 11/2005 | George | A61N 2/02 607/2 |
| 2006/0161039 A1 | 7/2006 | Juliana et al. | |
| 2006/0199992 A1* | 9/2006 | Eisenberg | A61N 1/40 600/14 |
| 2008/0058582 A1* | 3/2008 | Aho | A61N 2/02 600/13 |
| 2008/0262287 A1 | 10/2008 | Dussau | |
| 2009/0142724 A1 | 6/2009 | Rosenblood et al. | |
| 2009/0227830 A1* | 9/2009 | Pillutla | A61G 15/125 600/13 |
| 2011/0288365 A1* | 11/2011 | Zangen | A61N 2/02 600/13 |
| 2012/0157752 A1* | 6/2012 | Nishikawa | A61B 5/05 600/15 |
| 2013/0085316 A1* | 4/2013 | Fox | A61N 2/02 600/13 |
| 2014/0058189 A1* | 2/2014 | Stubbeman | A61N 2/002 600/13 |

FOREIGN PATENT DOCUMENTS

| | | | |
|---|---|---|---|
| WO | WO03082405 A1 | 10/2003 | |
| WO | WO2013166434 A1 | 11/2013 | |

* cited by examiner ical stimulation, TMS, for example, is
DEVICE SUPPORT APPARATUS

FIELD OF INVENTION

The present invention relates to positioning, fixing and/or moving devices with respect to persons seated in a chair.

BACKGROUND OF INVENTION

Performing precision operations with instruments requires that the instruments are accurately positioned with respect to whatever the operations are being performed on. transcranial magnetic stimulation, TMS, for example, is used to stimulate a small area inside a person's brain which requires that the magnetic coil used be positioned accurately, for shorter or longer periods of time, along the outside of the person's head. Similarly, for example, radiation therapy greatly benefits from aiming radiation patterns accurately at malignant cells to avoid damaging healthy tissue.

Using TMS as an example, a patient may be instructed to maintain his head immobile while a stimulating coil is moved along the outer surface of his head. If the coil is held accurately and reliably at the correct location, the stimulating effect can be aimed at a desired location inside the brain. On the other hand if the coil is inaccurately placed or accidentally moves, results of TMS are expected to be adversely affected.

TMS may be used, for example, to locate a person's motor threshold position, to facilitate rehabilitation following a stroke or to treat depression. Radiation therapy may be used to kill malignant cells. Using a manual placement technique, a treatment position on the patient's head or a position used to find a treatment position, such as the patient's motor threshold position, MTP, may be determined by moving a TMS coil near a predicted area determined by patient anatomical landmarks until the desired motor response is achieved.

US2009227830 describes an apparatus for positioning a medical instrument, such as a TMS coil, with respect to a patient.

SUMMARY OF THE INVENTION

According to a first aspect of the present invention, there is provided an apparatus, comprising a first arm configured to accept a device, the first arm comprising a first counterweight arrangement, a second arm supporting the first arm by a coupling, and a base defining a curve and having the second arm mounted thereon, wherein the second arm is movable along the curve, the base configured to be mounted on a chair.

In some embodiments, the first counterweight arrangement comprises that cabling of the device is attached to the first arm.

In some embodiments, the first counterweight arrangement comprises a display screen attached to the first arm.

According to a second aspect of the present invention, there is provided a system comprising an apparatus according to the first aspect attached to a chair, wherein the system is a transcranial magnetic stimulation system.

DETAILED DESCRIPTION OF EXEMPLARY EMBODIMENTS

Figure 1:
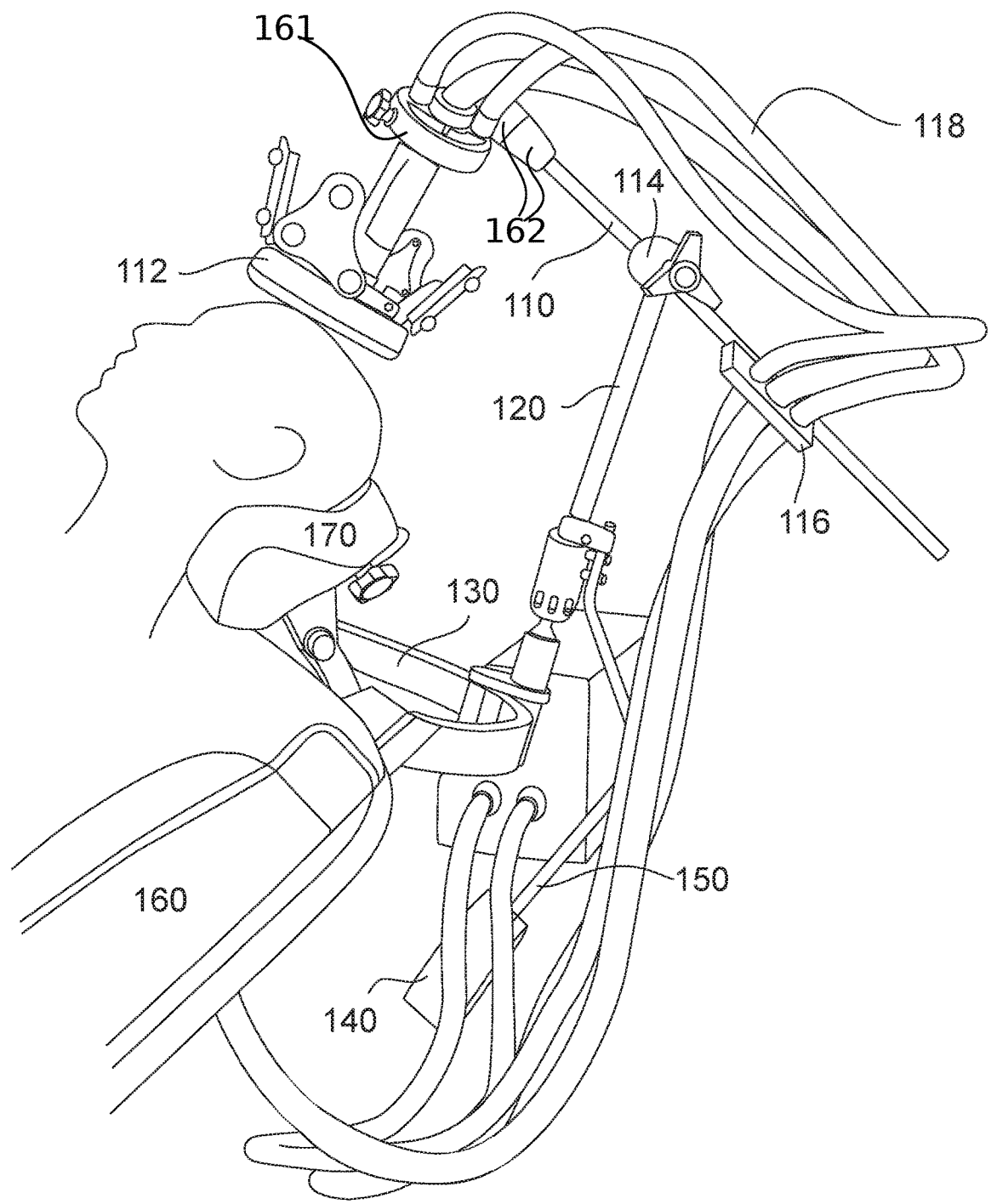
FIG. 1 illustrates an example apparatus in accordance with at least some embodiments of the invention.

FIG. 1 illustrates an example apparatus in accordance with at least some embodiments of the invention. The example of FIG. 1 may relate to a TMS system suitable for investigating anatomical features of a person's brain using electromagnetic fields, or treating the brain, for example. Illustrated is chair 160, which may comprise a reclining treatment chair suitable for TMS or radiation therapy, for example. On chair 160 is disposed headrest 170, which may be contoured to assist a person sitting in chair 160 to maintain his head immobile. To such effect, headrest 170 may be at least in part comprised of a material that accepts and retains a shape the back of a person's head, so the head can more easily be maintained stationary with respect to the chair.

An operator may place a TMS coil, for example, next to a person's head by hand and search for specific areas of the brain by monitoring for reactions responsive to magnetic stimuli. Holding a coil by hand for any period of time will tire the operator's hand even in case the coil is lightweight. When tired the operator becomes less capable of precisely holding the coil in place and the results of TMS are affected. Also in case a break is needed during a TMS session, continuing may be difficult in case the exact place where the session was interrupted is not immediately findable.

Accuracy requirements in TMS or radiation therapy may vary depending on the application. TMS may require an accuracy of at least 2 millimeters or 2 degrees, for example. An accuracy requirement of at least 2 millimeters may mean that a measurement needs to be capable of determining a position of device 112 with a measurement error of at most 2 millimeters. Alternatively, an accuracy requirement of 2 millimeters may mean that a location in a brain needs to be determined such that an error in the location in the brain is at most 2 millimeters. Accuracy requirements of radiation therapy may be substantially similar to this of TMS, as even larger tumours have edges that may be in direct contact with healthy tissue.

Device 112 may be operable to emit particulate or electromagnetic beams to the head of a person sitting in chair 160. Device 112 may comprise a TMS coil, wherein the coil may be enabled to generate an electromagnetic field at a distance from the coil inside the head. A TMS coil may be a coil winding device including a casing and contained in the casing coil windings of an electrically conductive material. A TMS system may comprise a computerized electromechanical instrument that produces and delivers brief duration rapidly alternating, or pulsed, magnetic fields to induce electrical currents directed at localized regions of the cortex. Device 112 may be powered by electrical cabling 118, which may be connected to electrical power and control devices. A TMS coil may be constructed to generate a magnetic field of known shape.

Cabling 118 may comprise one or more leads connecting device 112 to one or more units. Cabling 118 may provide to device 112 electrical energy and, optionally, control signals, for example signals to begin emitting electromagnetic radiation, or to cease emitting electromagnetic radiation. Cabling 118 may provide information of the functioning of device 112, for example cabling 118 may provide information on operational parameters of device 112.

Cabling 118 may provide information on error conditions device 112 may find itself in.

Device 112 is in the illustrated example mounted at a first end of first arm 110 on a device attachment portion, for example. An operator of device 112 may move device 112 along the surface of the person's head. First arm 110 may be supported on second arm 120 by coupling 114. Coupling 114 is configured to allow first arm 110 to move in a sliding manner through coupling 114, and/or coupling 114 may be configured to allow first arm 110 to rotate about a section of first arm 110 attached to coupling 114. In general the coupling may be arranged to provide for one or more than one degree of freedom of movement for the first arm with respect to the second arm. Device 112 may be attached to the first end of first arm 110 and/or the device attachment portion via a ball joint, for example, to provide for degrees of freedom for maneuvering device 112 along the surface of the head. The ball joint may be lockable individually. The ball joint may be electrically lockable by a mechanism wherein a single actuator is configured to lock all joints of the apparatus. In some embodiments, coupling 114 comprises a ball joint, hinge or bearing.

Attached to first arm 110 may be a connecting unit 116. Connecting unit 116 may be arranged to provide for a connection of cabling 118, so that the weight of cabling 118 forms a counterweight to the weight of device 112 with respect to coupling 114. Connecting unit 116 may be referred to as a cable attachment portion. This makes moving device 112 easier and lighter, which provides for improved accuracy in radiation treatment or TMS. An operator's hand becomes less tired when holding and moving device 112 due to the counterweight. Additionally, should the operator let go of device 112, counterweighting may keep device 112 stationary. In other words, device 112 may be left in its position simply by letting go of it which may decrease positioning errors what would otherwise occur due to involvement of human interaction. Coupling 114 may be adjusted to provide for a suitable stiffness to keep first arm 110 stationary in case an operator lets go of device 112 or first arm 110.

Connecting unit 116 may be slidably movable along first arm 110 to enable adjustment of the first counterweight arrangement. Additionally or alternatively, connecting unit 116 may enable an operator to adjust the counterweighting by fixing the cabling 118 at different points moving more or less of the cabling to one or the other side of connecting unit 116. Adjusting the counterweight may be useful in case devices 112 of differing weights are used, for example if coils of different weights are used. Adjusting the counterweight may also be useful in case operators with different preferences use the apparatus. Connecting unit 116 may be disposed at an end of the first arm that is opposite to the end of the first arm where the device attachment portion and/or device is disposed.

Alternatively to cabling 118, first arm 110 may be furnished with a different counterweight, such as for example a weight attached to first arm 110 to counter the weight of device 112. In some embodiments, first arm may be furnished with a display screen, or a combination of display screen and at least part of cabling 118 acting as a counterweight to device 112. The display screen may be configured to display operational parameters of device 112 to an operator. In embodiments where cabling 118 is at least in part connected to such a display screen, the display screen may obtain information concerning the operating parameters directly from the cabling. Thus counterweighting may be provided by the display screen and attached cabling, and an operator is enabled to observe operational parameters of device 112 from the screen acting as counterweight.

Mounted on chair 160, or alternatively on headrest 170, is base 130. Base 130 defines a curve, which may comprise that base 130 comprise a curved support or rail mounted or mountable on chair 160 or headrest 170. Chair 160 may comprise a back portion and a seat portion, and wherein a base may be attached to a portion of the chair, for example to the back portion. The length of the curve may proceed in a plane, in some embodiments the plane may be parallel to the plane defined by floor level, that is, horizontal. When the length of the curve proceeds in a single plane, the curve spans, that is defines, that plane. Second arm 120 is in the example of FIG. 1 mounted on base 130 in a movable way, for example so that the attachment point of second arm 120 to base 130 may be moved along the length of the curve. Moving the attachment point along the length of the curve may enable positioning of device 112 to different sides of the head. Moving the attachment point of second arm 120 to base 130 along the length of the curve may comprise moving the point along a rail that forms the curve of base 130. A rail in the form of a curve may be referred to as a rail in the shape of an arc. The ends of the arc may be attached at or near opposite corners of a top back portion of the chair. The second arm may remain in the same point of the curve in case the operator lets go of it. The base may be adjustably attached to a portion of the chair such that the base can be adjusted to a substantially horizontal orientation independently of the orientation of the portion of the chair to which it is attached. In some embodiments, counterweighting may be at least in part comprised of an actuator configured to move, or cause to move, the second arm along the curve and an actuator configured to lock at least the coupling The movement of the attachment point of second arm 120 to base 130 may be motorized, for example where base 130 comprises a horizontal curved rail, a suitable electric motor may be employed to move second arm 120 along the length of the curve of the rail. In some embodiments, also coupling 114 may be operable by a suitable motor. In some embodiments, the first arm further comprises a device attachment portion 161 configured to hold device 112. The device attachment portion may be connected to the first arm by a first joint or first joints which allow movement of the device attachment portion in one, two or three degrees of freedom with respect to the first arm. This may allow, for example, rotating device 112. The first joint or joints 162 may be driven by suitable motors, for example electric motors, to provide for automated and highly reliable positioning of device 112. The first joint or first joints 162 may be selectively lockable and/or their mobility is adjustable with respect to at least one degree of movement between the first arm and the device attachment portion.

Mounting base 130 on chair 160 facilitates obtaining improved results from TMS or radiation therapy, as inadvertent movement of chair 160 will not result in movement of device 112 relative to the head. This is in contrast to solutions where the chair and the device are supported on a floor independently of each other. In these solutions, if either the chair or the device is inadvertently moved, the device will move relative to the head. Mounting base 130 on chair 160 also provides the advantage that the first and second arms may be built shorter, which inherently increases the accuracy of pointing as longer parts are more difficult to position accurately. Base 130 may be mounted on a back portion of the chair, for example. Alternatively, if base 130 is mounted on a headrest portion of the chair, the device may remain essentially immobile with respect to a head resting on the headrest in case the headrest is adjusted. A camera may be mounted on a back portion or headrest portion of the chair. Such a camera may be used to position device 112 in a correct place with respect to the head, for example by employing machine-readable visual cues attached to the head and device 112. Mounted on the chair, the camera does not move relative to the head in case the chair moves. Mounted on the headrest, the camera does not move with respect to the head in case the headrest is adjusted. In general, instead of a camera, an imaging and/or tracking device may be used.

Second arm 120 may be mounted on base 130 in a rotatable way, so that in addition to being able to be moved along the length of the curve, the angle between second arm 120 and a plane spanned by the shape of the curve may be modified. This may be achieved by providing a joint or hinge in a mechanism attaching second arm 120 to base 130. Such rotation may provide for a tilt of the apparatus comprising the first arm, second arm and device 120 toward and away from the head. To stabilize this rotation, a second counterweight may be provided, which is illustrated in FIG. 1 as counterweight 140.

Counterweight 140 is suspended below base 130 and connected to second arm 120 by means of rigid third arm 150. Third arm 150 may be fixed to second arm 120 near the attachment point of second arm 120 to base 130, for example. Counterweight 140 may provide a benefit regarding the tilt of second arm 120, when an operator releases his grip of device 112, device 112 remains in place and doesn't move. To ensure this happens, this tilt of second arm 120 may be arranged with a suitable stiffness. The position of counterweight 140 on third arm 150 may be adjustable to provide for uniform counterweighting at different tilt angles.

Although illustrated as a separate weight, in some embodiments counterweight 140 is arranged using cabling 118. In some embodiments, cabling 118 is used to both provide the counterweighting at connecting unit 116 and counterweight 140. When cabling 118 is used in counterweight 140, counterweight 140 may comprise a connecting unit through which cabling 118 may traverse, and the connecting unit may allow an operator to adjust the counterweighting by fixing the cabling 118 at different points moving more or less of the cabling to one or the other side of the connecting unit.

As a result of the first counterweight provided at connecting unit 116 and second counterweight 140, device 140 may be stabilized in the sense that it is light to move in at least two degrees of freedom and additionally will remain in place in case an operator releases his grip of device 112. Locking movable couplings s, hinges or joints requires less force when the apparatus is counterweighted with respect to the coupling, hinge or joint in question. Operating device 112 becomes possible with one hand when device 112 is counterweighted.

Using at least one counterweight and/or lockable couplings, bearings, hinges and joints facilitates obtaining improved results from TMS or radiation therapy, as inadvertent movement of device 112 may be reduced or avoided. In addition to improved results, sessions of TMS or radiation therapy may be shorter in duration where positioning is improved by providing a stabler device 112. In addition or alternatively to being lockable, any couplings, bearings, hinges and joints may be capable of providing adjustable or partly restricted movement. Adjustable or partly restricted movement may comprise, for example, that movement requires more force.

Movable parts of the apparatus of FIG. 1 may be lockable from a single actuator. In this case, an operator may use one hand to place device 112 to a desired position and activate the locking actuator with his other hand to lock device 112 into place. Said movable parts, comprising coupling 114, attachment of second arm 120 to base 130 and tilt of second arm 120, may be locked with electrical servos, solenoids, brake wires or linear actuators, for example.

Figure 2:
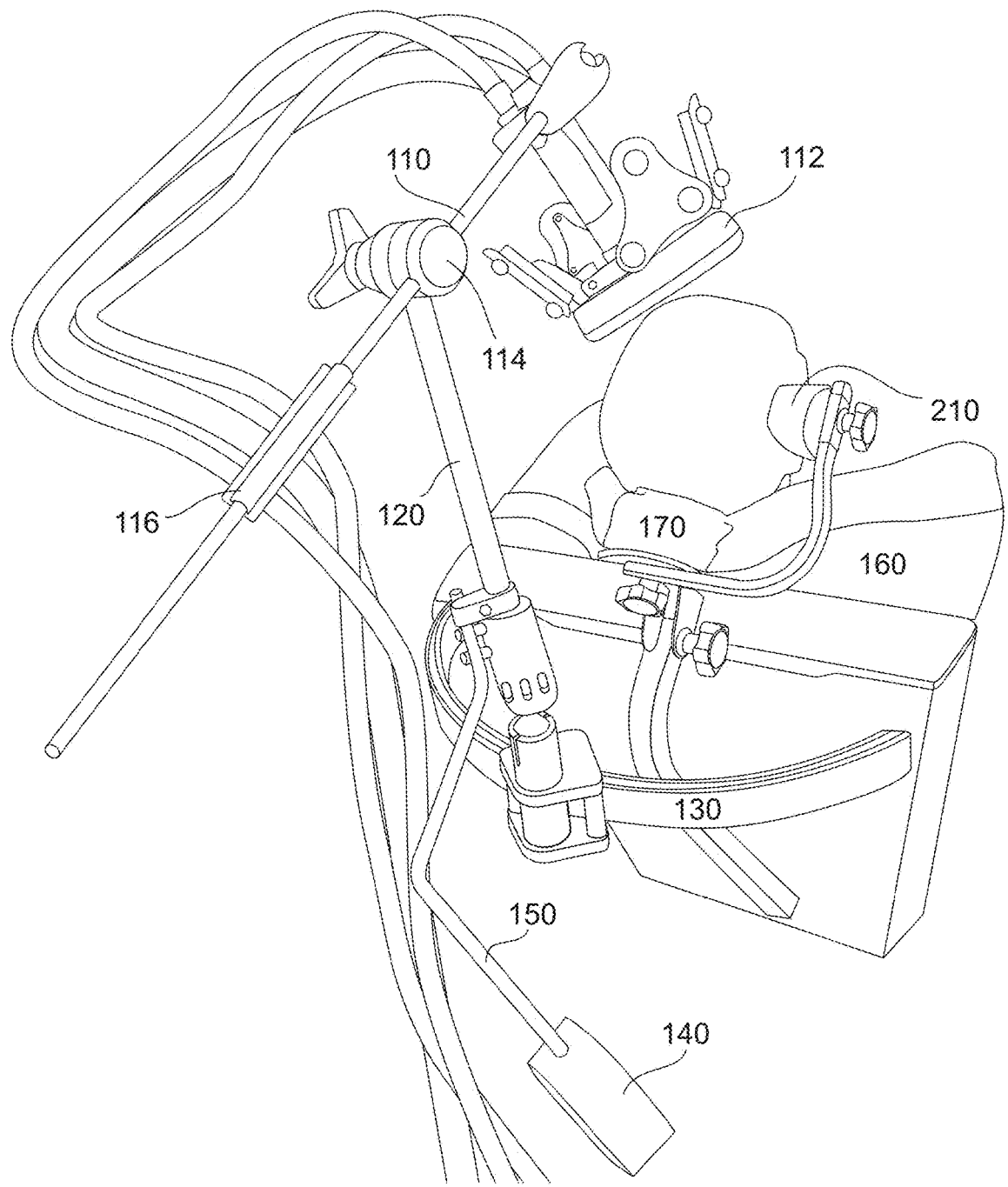
FIG. 2 illustrates the example apparatus of FIG. 1 from a different perspective.

FIG. 2 illustrates the example apparatus of FIG. 1 from a different perspective. Like numbers denote like structures as in FIG. 1. Head support 210, which was absent in FIG. 1, is present in FIG. 2 since it is visible from the perspective used in FIG. 2. Head support 210 provides for stabilizing the head further on headrest 170. In some embodiments head supports 210 are provided, one on each side of the head to help immobilize the head. In these cases, at least one of the two head supports 210 may be adjustable. Head support 210 may comprise a sanitary, soft surface for hygienically, safely and comfortably supporting a head.

Figure 3:
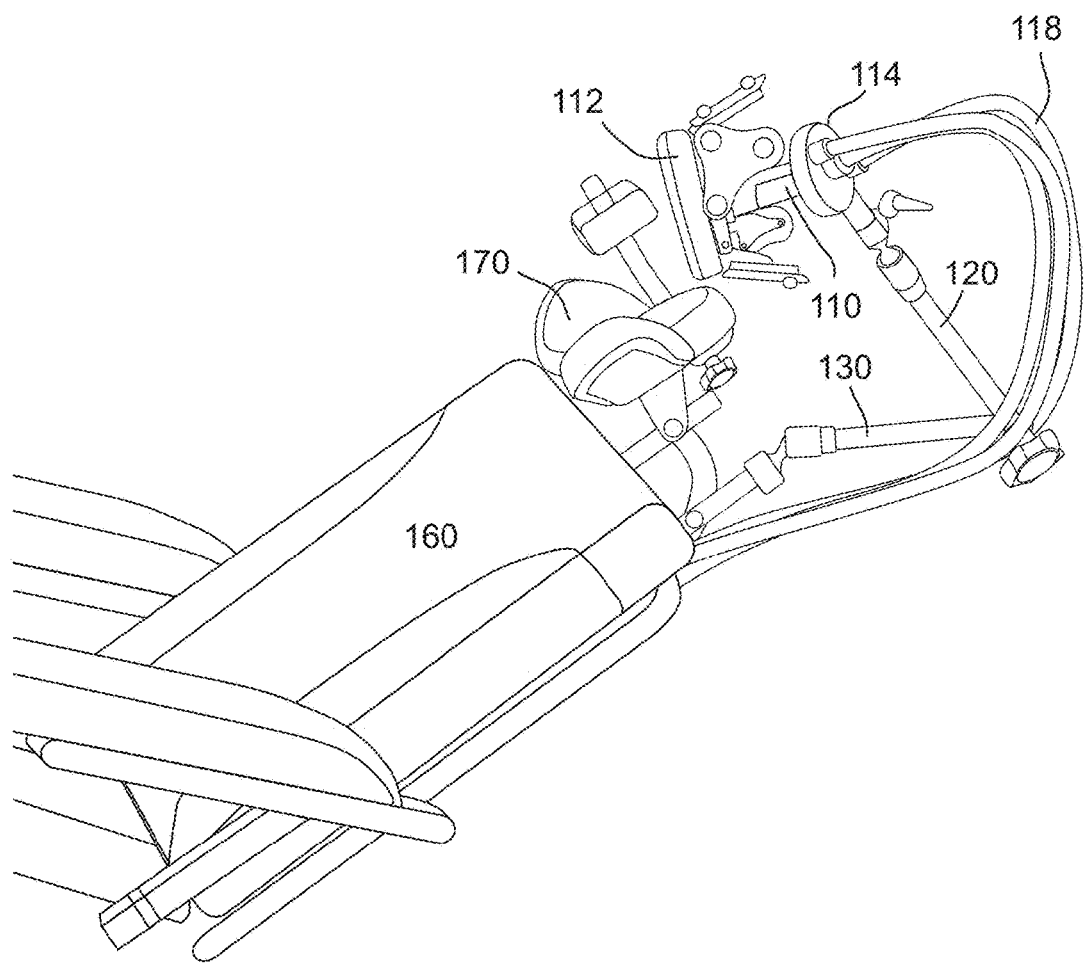
FIG. 3 illustrates another example apparatus in accordance with at least some embodiments of the invention.

FIG. 3 illustrates another example apparatus in accordance with at least some embodiments of the invention. Like numbers denote like structures as in FIGS. 1 and 2. A difference to the embodiment illustrated in FIG. 1 is in the structure of base 130. Instead of a curved structure, in the embodiment of FIG. 3 base 130 takes the form of a base arm 130. Base arm 130 is rotatably attached to chair 160 so that the end of base arm 130 that is not attached to chair 160 can sweep a curve, thus defining the curve. The swept curve may be in a plane parallel to floor level, for example. Second arm 120 is in this embodiment attached to or near the end of base arm 130 that can sweep the curve, thus enabling second arm 120 to move in a similar way to the second arm 120 in the embodiment illustrated in FIG. 1. Also in the embodiment of FIG. 3, second arm 120 may be enabled to tilt with respect to a plane spanned by the curve. Also in the embodiment of FIG. 3, counterweights may be provided as in FIG. 1 to the tilt of second arm 120 with respect to a plane spanned by the curve and the movement of first arm 110 with respect to second arm 120 provided by coupling 114.

Although described above in terms of a chair, in some embodiments base 130 may be mounted or mountable on a bed, such as for example a hospital bed. Base 130 may be attached to a portion of a frame of the bed, for example. This provides the benefit that persons who are in too poor a condition to sit in a chair may be treated with the device.

In general there is provided an apparatus, comprising a first arm configured to accept a device, the first arm comprising a first counterweight arrangement, a second arm supporting the first arm by a coupling, the second arm supporting a second counterweight arrangement, and a base defining a curve and having the second arm mounted thereon, wherein the second arm is movable along the curve, the base configured to be mounted on a chair.

The device may comprise a TMS coil, for example. The first counterweight arrangement may comprise a connecting unit enabled to accept attachment of cabling used to power and/or control the device, for example.

The second counterweight arrangement may comprise a connecting unit enabled to accept attachment of cabling used to power and/or control the device, for example. In first and second counterweight arrangements may both be enabled to accept attachment of cabling used to power and/or control the device to provide counterweighting. Alternatively, at least one of the first and second counterweight arrangements may comprise a weight other than the cabling used to power and/or control the device. At least one of the first and second counterweight arrangements may comprise both cabling and a separate weight.

The base may be at least in part formed in the shape of the curve. Alternatively, the base may comprise a base arm, the base arm defining the curve by being at one end rotatably fixed to the chair and the curve being formed by movement of the other end. Where the base is formed in the shape of a curve, it may comprise a rail. Such a rail may be mounted on a chair or bed at two points, for example at both ends. Such a rail may be semicircular or semi-elliptical in shape, for example.

The coupling may be configured to provide a rotating or sliding movement for the first arm with respect to the second arm. The coupling may comprise a ball joint.

The second counterweight arrangement may comprise a weight arranged below the base by a third arm, the third arm being mounted at one end on the second arm and the third arm supporting the weight at the other end. The second counterweight arrangement may counterweight a tilting of the second arm with respect to a plane spanned by the shape of the curve.

The first arm, second arm, third arm, base and/or base arm may be constructed of a suitable rigid material to allow for reliable positioning of device 112 when moving parts are locked. For example, the arms may be metallic pipes built of stainless steel or aluminum.

In some embodiments at least one of the first arm, second arm, third arm, base and/or base arm are constructed of non-magnetic material to minimize any effects on a shape of a magnetic field generated by device 112. Examples of suitable non-magnetic materials include plastic and graphite.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. An apparatus, comprising:
a first arm configured to accept a transcranial magnetic stimulation device, the first arm comprising a first counterweight arrangement;
a second arm supporting the first arm by a coupling;
a base comprising a curved portion and having the second arm mounted directly on the curved portion at an attachment point, wherein the curved portion is at least in part formed in the shape of a curve, the attachment point being configured to move along a length of the curve of the curved portion while remaining directly mounted on the curved portion, the shape of the curved portion enabling movement of the transcranial magnetic stimulation device to different sides of a head, the base configured to be mounted on a chair.

2. The apparatus according to claim 1, wherein the apparatus further comprises the transcranial magnetic stimulation device lockably attached to the first arm.

3. The apparatus according to claim 2, wherein the first counterweight arrangement comprises cabling of the device attached to the first arm, the coupling being between the device and the section of the first arm where the cabling is attached.

4. The apparatus according to claim 3, wherein the cabling is attached to the first arm via a connecting unit, the connecting unit being slidably movable along the first arm to enable adjustment of the first counterweight arrangement.

5. The apparatus according to claim 1, wherein the second arm supports a second counterweight arrangement.

6. The apparatus according to claim 5, wherein the second counterweight arrangement comprises a weight arranged below the base by a third arm, the third arm being mounted on the second arm and the third arm supporting the weight at an end.

7. The apparatus according to claim 1, wherein the first arm further comprises a device attachment portion configured to hold the transcranial magnetic stimulation device in a locked position and orientation with respect to the device attachment portion.

8. The apparatus according to claim 7, wherein the device attachment portion is connected to the first arm by a first joint or first joints which allow movement of the device attachment portion in three degrees of freedom with respect to the first arm.

9. A system for Transcranial Magnetic Stimulation (TMS) comprising;
a TMS coil device having at least one cable extending therefrom, a first arm having a device attachment portion at one end configured to lockably receive the TMS coil device, said first arm further having a cable attachment portion configured to receive the at least one cable extending from the TMS coil device;

a second arm supporting the first arm by a coupling;

a base comprising a curved portion and having the second arm mounted directly on the curved portion at an attachment point, wherein the curved portion is at least in part formed in the shape of a curve, the attachment point being configured to move along a length of the curve of the curved portion while remaining directly mounted on the curved portion, the shape of the curved portion enabling movement of the transcranial magnetic stimulation device to different sides of a head, said base configured to be mounted on a portion of a chair or bed.

10. The system according to claim 9, wherein the device attachment portion is configured to hold the device in a locked position and orientation with respect to the device attachment portion.

11. The system according to claim 10, wherein the device attachment portion is connected to the first arm by a first joint, or first joints, which allow movement of the device attachment portion in three degrees of freedom with respect to the first arm.

12. The system according to claim 11, wherein the first joint or first joints are selectively lockable and/or their mobility is adjustable with respect to at least one degree of movement between the first arm and the device attachment portion.

13. The system according to claim 9, wherein the coupling is selectively lockable and/or mobility of the coupling is adjustable with respect to at least one degree of movement between the first arm and the second arm.

14. The system according to claim 9, wherein the cable attachment portion is configured to act as a counterweight to the TMS coil device while the TMS coil device is lockably attached to the first arm and the at least one cable extending from the TMS coil device is attached to the cable attachment portion on the first arm.

15. The system according to claim 9, wherein the cable attachment portion is adjustable along at least a portion of a length of the first arm.

16. The system according to claim 9, wherein the cable attachment portion is located at an end of the first arm opposite from the device attachment portion.

17. The system according to claim 9, wherein the base comprises a rail attached at or near opposite corners of a top back portion of the chair.

18. The system according to claim 9, further comprising a counterweight portion attached to the second arm and located at least partially below the base.

19. The system according to claim 9, further comprising the chair with a back portion and a seat portion, and wherein the base is attached to a portion of the chair.

20. The system according to claim 19, wherein the base is adjustably attached to a portion of the chair in such a way that the base portion can be adjusted to a substantially horizontal orientation independently of the orientation of the portion of the chair to which the base is attached.

21. A system for Transcranial Magnetic Stimulation (TMS) comprising:

a TMS coil device having at least one cable extending therefrom, a chair with a back portion and a seat portion, a first arm having a device attachment portion at one end configured to lockably receive the TMS coil device, said first arm further having a cable attachment portion configured to receive the at least one cable extending from the TMS coil device;

a second arm supporting the first arm by a coupling;

a base attached to a portion of the chair, said base comprising a curved portion and having the second arm mounted directly on the curved portion at an attachment point, wherein the curved portion is at least in part formed in the shape of a curve, the attachment point being configured to move along a length of the curve of the curved portion while remaining directly mounted on the curved portion, the shape of the curved portion enabling movement of the transcranial magnetic stimulation device to different sides of a head.

* * * * *